(12) United States Patent
Kudyakov (10) Patent No.: US 10,267,766 B2
(45) Date of Patent: Apr. 23, 2019

(54) MULTI-LAYER EDDY CURRENT PROBE, METHOD FOR PRODUCING A MULTI-LAYER EDDY CURRENT PROBE, AND TEST UNIT COMPRISING A MULTI-LAYER EDDY CURRENT PROBE

(71) Applicant: Magnetische Prüefanlagen GmbH, Reuttingen (DE)

(72) Inventor: Timur Kudyakov, Tuebingen (DE)

(73) Assignee: Magnetische Pruefanlagen GmbH, Reutlingen (DE)

( * ) Notice: Subject to any disclaimer, the term of this patent is extended or adjusted under 35 U.S.C. 154(b) by 430 days.

(21) Appl. No.: 14/911,945

(22) PCT Filed: Aug. 1, 2014

(86) PCT No.: PCT/EP2014/066660
§ 371 (c)(1),
(2) Date: Feb. 12, 2016

(87) PCT Pub. No.: WO2015/022210
PCT Pub. Date: Feb. 19, 2015

(65) Prior Publication Data
US 2016/0195497 A1 Jul. 7, 2016

(30) Foreign Application Priority Data

Aug. 13, 2013 (DE) ........................ 10 2013 216 019

(51) Int. Cl.
*H02J 1/00* (2006.01)
*G01N 27/90* (2006.01)
(Continued)

(52) U.S. Cl.
CPC .......... *G01N 27/9033* (2013.01); *G01R 3/00* (2013.01); *H05K 1/165* (2013.01); *H05K 3/30* (2013.01);
(Continued)

(58) Field of Classification Search
CPC ........ H01L 21/00; H01L 2221/00; H02J 1/00; H01F 1/00
See application file for complete search history.

(56) References Cited

U.S. PATENT DOCUMENTS 5,111,412 A 5/1992 Toernblom
5,389,876 A 2/1995 Hedengren et al.
(Continued)

FOREIGN PATENT DOCUMENTS

DE 298 03 750 U1 7/1999
DE 20 2004 002 448 U1 5/2005
(Continued)

OTHER PUBLICATIONS

German Office Action issued in counterpart German Application No. 10 2013 216 019.4 dated Nov. 14, 2016 (five pages).
(Continued)

*Primary Examiner* — Jermele M Hollington
*Assistant Examiner* — Temilade S Rhodes-Vivour
(74) *Attorney, Agent, or Firm* — Crowell & Moring LLP (57) ABSTRACT

A multi-layer eddy current probe has a large number of flat spiral coils which are arranged in different coil layers of a multi-layer arrangement, wherein a respective insulating layer which is composed of electrically insulating material is arranged between adjacent coil layers of the multi-layer arrangement. Each of the flat coils has an inner terminal and an outer terminal. Selected terminals of selected flat coils of different coil layers are electrically connected to one another by way of vias. The flat coils form at least one coil group which has at least three flat coils which are arranged one above the other in different layers, wherein the inner terminals of the at least three flat coils of the coil group are electrically conductively connected by means of a common inner via.

15 Claims, 4 Drawing Sheets

(51) Int. Cl.
*H05K 1/16* (2006.01)
*G01R 3/00* (2006.01)
*H05K 3/30* (2006.01)
*H05K 3/40* (2006.01)
*H01L 21/00* (2006.01)
*H01F 1/00* (2006.01)

(52) U.S. Cl.
CPC ............ *H05K 3/4038* (2013.01); *H01F 1/00* (2013.01); *H01L 21/00* (2013.01); *H01L 2221/00* (2013.01); *H05K 2201/09672* (2013.01)

(56) References Cited

U.S. PATENT DOCUMENTS

| | | | | |
|---|---|---|---|---|
| 6,002,320 | A * | 12/1999 | Uda | H01F 5/00 29/602.1 |
| 6,888,347 | B2 * | 5/2005 | Batzinger | G01N 27/9033 324/240 |
| 2005/0184729 | A1 * | 8/2005 | Johnson | G01N 27/9006 324/239 |
| 2006/0132123 | A1 * | 6/2006 | Wang | G01N 27/902 324/239 |
| 2009/0115411 | A1 | 5/2009 | Sun et al. | |
| 2012/0249281 | A1 | 10/2012 | Campbell et al. | |
| 2013/0241541 | A1 * | 9/2013 | Endo | G01N 27/87 324/232 |

FOREIGN PATENT DOCUMENTS

| | | |
|---|---|---|
| DE | 10 2012 102 725 A1 | 10/2012 |
| EP | 0 035 964 A1 | 9/1981 |
| EP | 0 512 796 B1 | 8/1997 |
| EP | 1 885 019 A1 | 2/2008 |
| EP | 0 256 103 B1 | 7/2011 |

OTHER PUBLICATIONS

International Search Report (PCT/ISA/210) issued in PCT Application No. PCT/EP2014/066660 dated Oct. 13, 2014 with English-language translation (six (6) pages).
German-language Office Action issued in counterpart German Application No. 10 2013 216 019.4 dated Jun. 11, 2014 (six (6) pages).

* cited by examiner

MULTI-LAYER EDDY CURRENT PROBE, METHOD FOR PRODUCING A MULTI-LAYER EDDY CURRENT PROBE, AND TEST UNIT COMPRISING A MULTI-LAYER EDDY CURRENT PROBE

BACKGROUND

The invention relates to a multi-layer eddy current probe for use in an eddy current test unit for non-destructive testing of electrically conductive materials, to a method for producing a multi-layer eddy current probe of this kind, and to an eddy current test unit comprising at least one multi-layer eddy current probe of this kind.

Eddy current testing has proven successful for non-destructive testing (NDT) of electrically conductive materials in many fields of application, for example for automated non-destructive testing on semi-finished products for the metal-producing and metal-processing industry, for carrying out tests on safety-related and functionally critical components for land vehicles and aircraft or in plant construction. The sensor systems employed or used for eddy current testing are usually called "eddy current probes".

During eddy current testing, an eddy current probe is arranged at a short test distance from a surface of a test object, which surface is under test. The test object comprises an electrically conductive material at least in the region of the surface. A relative movement between the test object and the eddy current probe is generally generated for testing purposes, for example by the eddy current probe moving over that region of the surface which is under test.

An eddy current probe which is constructed using coils comprises one or more field coils (or excitation coils) which are connected to an AC voltage source in order to carry out the test and can then produce a radiofrequency electromagnetic alternating field which, during testing, penetrates the test material and produces eddy currents substantially in a layer of the test material which is close to the surface, said eddy currents having a retroactive effect on one or more measuring coils (or receiver coils) of the eddy current probe due to mutual induction. A defect in the tested region, for example a crack, an impurity or another material inhomogeneity, interferes with the propagation of the eddy currents in the test material and therefore changes the eddy current intensity and as a result the intensity of the magnetic secondary field, which has a retroactive effect on the measuring coil, too. The resulting changes in impedance in a measuring coil lead to electrical measuring signals which can be evaluated by means of an evaluation unit in order to identify and to characterize defects. Eddy current probes in which the field coils (excitation coils) and the measuring coils, which are separate from said coils, are coupled by means of the material of the test object are called transformer-type eddy current probes.

Whereas older-generation eddy current probes were typically constructed with coils wound from wire, eddy current probes which can be produced using printed circuit board technology methods in the manner of printed circuits are additionally also used nowadays. Said eddy current probes include multi-layer eddy current probes of the generic type which have a multi-layer arrangement with a large number of flat spiral coils which are arranged in different coil layers of the multi-layer arrangement, wherein a respective insulating layer which is composed of an electrically insulating material is arranged between immediately adjacent coil layers.

Each of the flat coils has an inner terminal on the inner turn and an outer terminal on the outer turn of the flat coil. The terminals serve to electrically connect the flat coils to other flat coils or external components. In order to electrically connect flat coils from different layers to one another, selected terminals of selected flat coils of different coil layers are electrically connected to one another by means of vias. A via ("vertical interconnect access") is a vertical electrical connection, that is to say an electrical connection which runs substantially perpendicular to the layers, between flat coils in different coil layers. The connection can be realized, for example, by an internally metalized hole in the material of the insulating layer.

U.S. Pat. No. 5,389,876 (also see EP 0 512 796 B1) describes multi-layer eddy current probes which have a large number of identical flat coils which are encapsulated in a flexible, multi-layered integrated eddy current probe arrangement. One embodiment (FIGS. 6a and 6b) provides coil pairs with in each case two flat coils which are arranged one above the other in different coil layers. The turns of the two flat coils run with opposite winding senses in relation to one another. The inner terminals of the flat coils are connected to one another by means of a via. As a result, the flat coils of the coil pair are connected electrically in series, as a result of which a current flows through the turns of the two flat coils in the same circulation direction at a specified time, so that the fields of the two flat coils are added when an AC voltage is applied. In another embodiment (FIG. 8), two coil pairs of this kind are vertically interleaved one in the other such that a flat coil of a second coil pair is arranged between the flat coils of a first coil pair in the vertical direction. The associated flat coils of a coil pair are in each case connected by means of an inner via, which inner vias connect the inner terminals of the associated flat coils, so that in each case two vias pass through the turn-free inner regions of the two internal flat coils.

EP 2 056 103 B1 likewise describes flexible multi-layer eddy current probes with coil pairs which each comprise two flat coils which are arranged one above the other in different coil layers, wherein the turns of the two flat coils run with opposite winding senses in relation to one another and the inner terminals of the flat coils are connected to one another by means of a via.

PROBLEM AND SOLUTION

The invention is based on the problem of providing a multi-layer eddy current probe of the kind mentioned in the introductory part which can be produced in a relatively cost-effective manner and allows eddy current testing with a high degree of sensitivity, even to small defects.

A multi-layer eddy current probe according to embodiments of the invention, an eddy current test unit comprising a multi-layer eddy current probe of this kind, and also a method for producing a multi-layer eddy current probe of this kind are provided for solving said and other problems.

Advantageous developments are described and claimed herein. The wording of all of the claims is incorporated in the description by way of reference.

In a multi-layer eddy current probe according to the claimed invention, the flat coils form at least one coil group which has at least three flat coils which are arranged one above the other in different layers, wherein the inner terminals of the at least three flat coils of the coil group are electrically conductively connected by means of a common inner via.

A "flat coil" (also called "pancake coil") within the meaning of this application is a coil with turns which run in the form of a spiral in a manner situated one in the other in a common, flat or slightly curved area, wherein all of the turns of the flat coil are typically situated in this area. The turns surround an inner region which is free of turns. The inner terminal is situated on the inner region. The region which is covered by the turns of a flat coil plus the inner region is called the "coil area" here and can be characterized by an (outer) coil diameter. The turns can run in a continuously curved manner in order to obtain a more or less round or oval coil shape. Turns can also run in a rectilinear manner in sections and form corners, so that a polygonal coil shape, for example a square coil shape, is produced. A "coil group" has three or more flat coils which are arranged one above the other in a direction perpendicular to the layer extent ("vertical direction") in different coil layers and are electrically insulated from one another by intermediate insulating layers. The inner terminals of all of the flat coils which belong to the coil group are situated more or less one above the other and are electrically connected by means of a single common inner via.

When three or more flat coils of a (vertical) coil group are arranged one above the other, the effect of said flat coils in the region of the test object close to the surface adds up in a relatively small action region which depends, amongst other things, on the lateral extent of the flat coils or the coil areas and the number of turns accommodated therein. The flat coils of the coil group can be arranged in directly adjacent layers. However, it is also possible for one or more flat coils which do not belong to the coil group to be arranged between adjacent flat coils of a coil group. In this case, the inner via would also pass through the inner region of said flat coils, but without being electrically connected to the associated turns.

The common inner via allows two or more flat coils of the coil group, which flat coils act with the same winding sense, to be connected electrically in parallel using only one or two further vias. It is also possible for more than two, for example four or more, outer vias to be associated with a coil group. If the flat coils of the coil group are jointly connected to an AC voltage source of a power supply, they can be used as field coils (excitation coils). The fields of the at least three flat coils overlap and act at the same site of the test object. When it is ensured during the connection process that current with the same circulation direction flows through each of the flat coils at a specified time, the electromagnetic fields which are generated by the respective flat coils add up at the same site in the test object, so that a high local concentration of the excitation field strength can be achieved in the test object at the site of the coil group.

Since three or more flat coils of a coil group are electrically connected by means of a single common inner via, the number of vias in the inner region of a coil group can be reduced in comparison to the prior art. As a result, it is possible to reduce the size of the turn-free inner region of the flat coils or to use this to fit the turns, so that, owing to the use of parts of the inner region, it is possible to accommodate more turns in a flat coil in comparison to the prior art given the same outside diameter or the same coil area. This increases the number of turns which are related to the coil area, as a result of which stronger electromagnetic fields can be generated given the same excitation current, for example when said flat coils are used as field coils. As an alternative or in addition, it is also possible to produce flat coils with a smaller coil area given the same number of turns, as a result of which the local resolution of the eddy current probe can be increased.

The design allows a reduction in the number of vias in comparison to conventional multi-layer arrangements with a similar number of flat coils which are arranged one above the other. Production is rendered simpler and more cost-effective as a result. All of the flat coils of a coil group are preferably connected to the same inner via after production, and therefore only one single via of the coil group is arranged in an inner region, which is surrounded by turns, in each of the flat coils of the coil group. In addition, one or more vias of measuring coils can further run through the inner region.

In advantageous developments, the coil group has at least four flat coils which are arranged one above the other in different layers. It is possible to intensify the joint effect of the coils as a result. Flat coils of the coil groups can then also be combined to form a plurality of subgroups with in each case at least two flat coils, this allowing further advantages.

A coil group usually has an even number of flat coils, for example four, six or eight flat coils. In principle, the number of flat coils of a coil group does not have an upper limit but, for reasons of simple production, no more than 20 flat coils are arranged one above the other in general.

In some embodiments, at least two flat coils of the coil group, which flat coils are arranged in different layers, are connected electrically in parallel by means of the inner via and an outer via. If the turns of these flat coils, which are connected in parallel, run with the same winding sense, the electrical effects of said turns add up. It is possible for three, four or more flat coils to be connected in parallel in a space-saving arrangement.

Particular advantages can be achieved when flat coils of a coil group are subdivided into a plurality of subgroups. In some embodiments, this is realized by the flat coils of the coil group forming a first subgroup comprising at least two first flat coils and at least one second subgroup comprising at least two second flat coils, wherein the turns of the first flat coils run with the same winding sense as one another, and the turns of the second flat coils run with the same winding sense as one another and with the opposite winding sense to the turns of the first flat coils, and wherein furthermore outer terminals of the first flat coils are electrically conductively connected by means of a first outer via, and outer terminals of the second flat coils are electrically conductively connected by means of a second outer via. As a result, the effects of the flat coils of a subgroup each add up on account of parallel connection and, at the same time, the subgroups can be operated in a manner connected electrically in series by means of the inner via. During operation of this coil arrangement using an alternating current source with an adjustable current amplitude (current impression), a partial current is impressed on each of the flat coils, said partial current being greater than in the case of a circuit in which the same flat coils of the coil group are all connected in parallel to one another. The relatively large partial currents also mean that the fields which are generated are stronger, as a result of which excitation fields of greater intensity can be generated overall.

In a multi-layer arrangement according to the claimed invention, all of the vias of coil groups of the multi-layer arrangement can pass from a first side which is accessible for external contact-connection to an opposite second side which is accessible for external contact-connection. Production of the multi-layer arrangement is rendered substantially simpler and more cost-effective owing to a simplified design of this kind. In particular, it may be the case that the multi-layer arrangement does not have any buried vias and/or any blind contact-connections. A buried via is a non-continuous via in the interior of the multi-layer arrangement which butts against an insulating layer at both ends. Vias of this kind have to be produced before the delimiting insulating layers are applied, further coil layers possibly then being applied to said insulating layers. A blind via has a free end which can be used for making contact with the multi-layer arrangement from the outside, while the other (inner) end butts against an insulating layer. Blind vias are frequently located on the outer sides of multi-layer arrangements, which outer sides are accessible for external contact-connection.

A simplified method for producing a multi-layer eddy current probe of the kind mentioned in the introductory part can be carried out such that initially all of the coil layers and insulating layers which are situated between the coil layers are produced in a manner situated one above the other without through-plating between coil layers in such a way that a coil group is created at at least one location on the multi-layer arrangement, said coil group having at least three flat coils which are arranged one above the other in different layers and have inner terminals which are arranged one above the other, and that thereafter an inner via which passes from the first side to the second side is produced, said inner via connecting the inner terminals of all of the flat coils of the coil group. Therefore, it is not necessary to produce any vias, in particular any buried or blind vias, for the purpose of connecting the flat coils of the coil group, apart from for the purpose of generating the common, continuous via, as a result of which manufacture is simplified.

It may suffice for the eddy current probe or the multi-layer arrangement to have only one single coil group with three or more flat coils, which are connected by means of a common inner via, in different coil layers. However, the multi-layer arrangement is preferably produced such that it has a large number of coil groups of this kind which are arranged at a lateral distance next to one another in a one-dimensional or two-dimensional field arrangement. Arrangements of this kind are also called "coil arrays". A multi-layer arrangement can therefore have, for example, a row of coil groups which are arranged next to one another, in order to carry out testing over a relatively large test width which is several times larger than the coil diameter of the flat coils of a coil group. Therefore, test object surfaces can be tested over relatively large test widths at the same time as at a plurality of locations or along a plurality of relatively narrow paths. Two-dimensional field arrangements are also possible, said two-dimensional field arrangements having two or more rows of coil groups, which rows run parallel to one another, for example.

It is possible for all of the flat coils of a multi-layer arrangement to be used as field coils during operation, and for the eddy current probe to have one or more measuring coils or other magnetic field-sensitive sensors which are arranged separately from the multi-layer arrangement at another location, for example on the rear face of a test object, which rear face is situated opposite the multi-layer arrangement. However, one or more flat coils of the multi-layer arrangement are preferably used as measuring coils and accordingly are connected to an evaluation device during operation. The multi-layer arrangement preferably has one or more flat coils which can be used as measuring coils and are arranged substantially coaxially with flat coils of the coil group. By way of example, it is possible for at least one measuring coil to be arranged between two flat coils of a coil group. As an alternative or in addition, it is also possible for a flat coil which is used as a measuring coil to be arranged between adjacent insulating layers above the flat coils of a coil group or below the flat coils of a coil group. Flat coils which are used as measuring coils can likewise be electrically connected to one another by means of vias. These vias, which are associated with the measuring coils, can be routed through the inner region of flat coils of the coil groups in the case of coaxial arrangement. Connection of this kind is readily possible since only one single via is necessary for electrically connecting flat coils of a coil group, so that enough space for further vias (for measuring coils) remains in the inner region of the flat coils.

The invention also relates to an eddy current test unit comprising an electrical power supply and a coil arrangement of the kind described here which is connected to an output of the power supply. One or more coil groups can be connected to said power supply in order to serve as field coils. In advantageous embodiments, the power supply is designed to supply excitation current of a prespecifiable amplitude to flat coils of a coil arrangement, which flat coils are intended to be used as field coils, that is to say to operate them with current impression. The advantages of connecting flat coils in parallel can be optimally utilized as a result. The power supply can also operate such that a fixed operating voltage is prespecified for flat coils of (one or more) coil groups.

These and further features are apparent not only from the claims but also from the description and the drawings, wherein the individual features can be realized in each case by themselves or as a plurality in the form of subcombinations in an embodiment of the invention and in other fields and can constitute advantageous and inherently protectable embodiments. Exemplary embodiments of the invention are illustrated in the drawings and will be explained in greater detail in the text which follows.

DETAILED DESCRIPTION OF PREFERRED EMBODIMENTS

Figure 1:
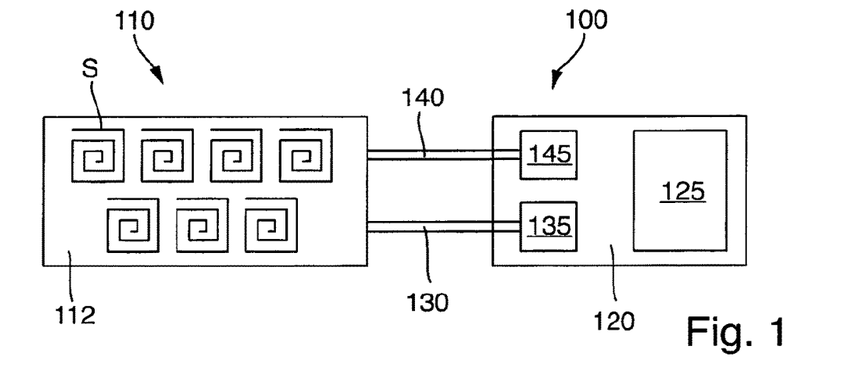
FIG. 1 shows an eddy current test unit comprising a multi-layer eddy current probe according to one embodiment of the invention.

FIG. 1 shows a schematic plan view of an eddy current test unit 100 according to one embodiment of the invention. The eddy current test unit has a multi-layer eddy current probe 110 which is electrically connected to a supply and evaluation unit 120 by means of an excitation current line 130 and a measuring signal line 140.

A central component of the multi-layer eddy current probe 110 is a multi-layer coil arrangement 112 which is constructed from a large number of material layers which are situated one above the other, a large number of flat spiral coils S, which form a coil array comprising two parallel rows of flat coils which are situated one above the other in the example, being integrated in said multi-layer coil arrangement. The flat coils can be operated, for example, at the same time or with a time delay by means of multiplexers.

The layer structure is explained in greater detail with reference to FIG. 2. Said figure shows a schematic vertical section through the multi-layer coil arrangement 112 at the site of a stack of flat coils which are situated vertically one above the other. Here, the term "vertically" means a direction perpendicular to the extent of the layers which are situated one above the other.

The multi-layer coil arrangement 112 which is constructed using printed circuit board technology has coil layers 114 which are composed of electrically conductive material and also has insulating layers 116 which are composed of electrically insulating material, which are situated between the coil layers and which electrically insulate the conductive structures of the coil layers from one another. The flat coils S1 to S4 are realized in the form of printed conductor tracks within the coil layers 114. Any electrical connections of flat coils within the same coil layer are also in the form of printed conductor tracks.

Figure 3A:
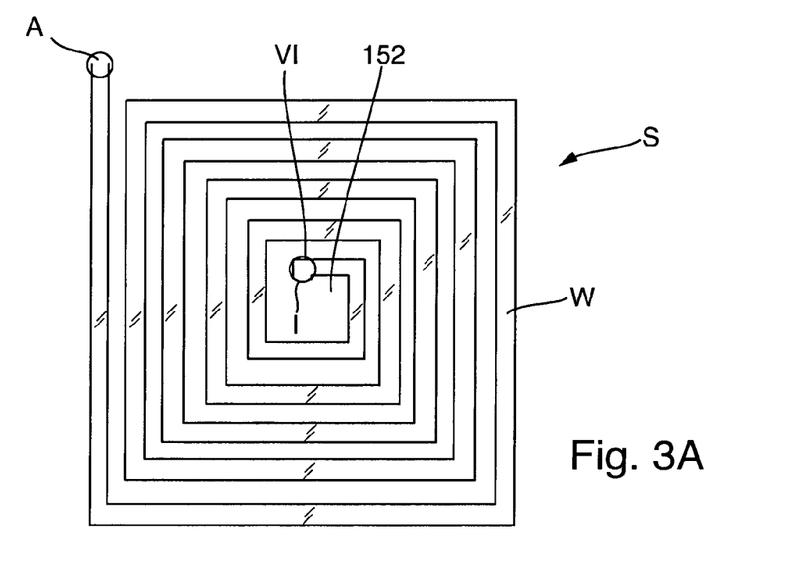
FIGS. 3A and 3B show, in FIG. 3A, a plan view of a flat coil in one embodiment of the invention and, in FIG. 3B, a reference flat coil from the prior art with the same coil diameter for comparison purposes.

As is schematically illustrated in FIG. 3A, the turns W of a flat coil S lie in a common plane and run in a spiral manner between an outer terminal A and an inner terminal I which is situated in the interior of the flat coil. An inner region 152 which is free of turns remains in the center of the regions which are occupied by turns. The inner terminal is situated on or in this inner region.

The flat coils of the multi-layer coil arrangement 112 can be subdivided into two groups with different functions. A first number of flat coils serves to excite the electromagnetic field which is intended to penetrate the test object P and produce eddy currents there. These flat coils are called excitation coils or field coils and are connected to an AC voltage source 135 by means of the excitation current line 130, said AC voltage source being designed in the example to supply alternating current of a prespecifiable maximum amplitude of the current intensity—which maximum amplitude can be adjusted in a continuously variable manner or in steps possibly using adjustment means—to the field coils (current impression).

The other group of flat coils which are electrically insulated from the field coils serve as measuring coils of the multi-layer eddy current probe 110 and are connected to an evaluation device 145 of the supply and evaluation unit 120 by means of the measuring signal line 140. Results of the eddy current test can be indicated by means of an indicator device 125 which, in the example, is integrated into the supply and evaluation unit 120, but can also be provided as a separate unit.

The field coils and the measuring coils are electrically insulated from one another, but are inductively coupled by means of the test object during testing (transformer-type eddy current probe).

Figure 2:
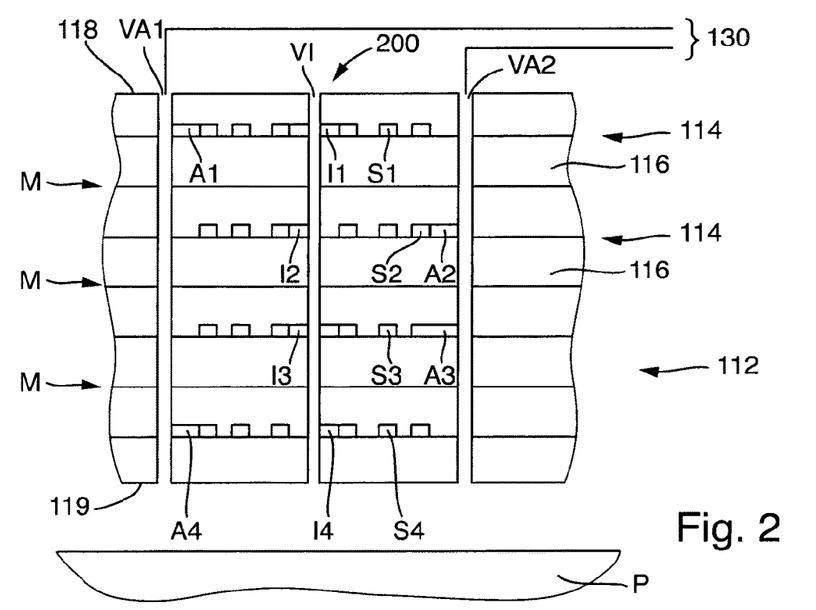
FIG. 2 shows a schematic vertical section through the multi-layer coil arrangement at the site of a stack of flat coils of a coil group, which flat coils are situated vertically one above the other.

The vertical section in FIG. 2 shows, by way of example, the electrical connection of four flat coils S1 to S4 which are arranged vertically one above the other in different coil layers and together form a (vertical) coil group 200 which serves as a group of field coils for field generation at the site of the coil group. The turns of the first flat coil S1, which is situated closest to the top face 118, run between the outer terminal A1 and the inner terminal I1 in the clockwise direction as viewed from the top face. The turns of the fourth flat coil S4, which is situated closest to the bottom face 119, run between the outer terminal A4 and the inner terminal I4 of said fourth flat coil with the same winding sense as said turns of the first flat coil. In the flat coils situated between said first flat coil and said fourth flat coil (second flat coil S2 and third flat coil S3), the turns run with the opposite winding sense to said turns of the first flat coil, and therefore the second and the third flat coil each have an identical winding sense, the first and the fourth flat coil each have an identical winding sense, and the turns of the first and the fourth flat coil run with the opposite winding sense to the turns of the second and the third flat coil.

The turns of the first and the fourth flat coil, which turns run with the same winding sense as one another, are each connected to a common first outer via VA1. The outer terminals A2 and A3 of the inner flat coils (second and third flat coil) which run with the opposite winding sense to said turns of the first and the fourth flat coil are each electrically connected to a second outer via VA2. All of the inner connection ends I1 to I4 of the coil group are jointly electrically connected to an inner via VI which runs through the inner regions of the flat coils. All three of the vias VA1, VA2 and VI each pass from the free top face 114 to the free bottom face 116. No buried vias or blind vias are required for connecting the flat coils of the coil group. The outer vias VA1 and VA2 are connected to the outputs of the AC voltage source 135 by means of conductors of the excitation current line 130.

In the multi-layer coil arrangement 112, measuring coils can be arranged, inter alia, between the field coils S1 to S4 and coaxially with said field coils in the coil layers which are designated M. The measuring coils are not illustrated for reasons of clarity. Said measuring coils can have any desired shape and size. Measuring coils can be designed as absolute coils or differential coils. Combinations of absolute coils and differential coils are often useful.

Figure 4A:
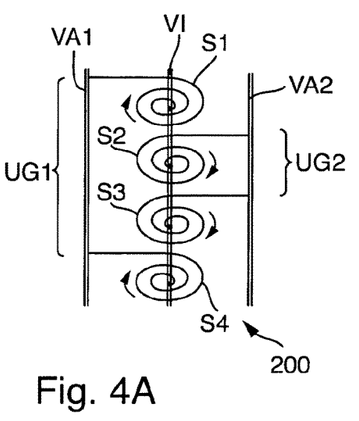
FIGS. 4A and 4B show, in FIG. 4A, a simplified, schematic illustration of the electrical connection of the flat coils from FIG. 2 and, in FIG. 4B, a schematic circuit diagram of the same coil arrangement.
Figure 4B:
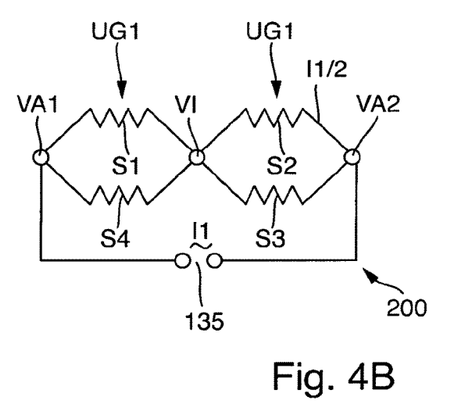

In order to further explain the design and function of the coil group 200 from FIG. 2, FIG. 4A shows a simplified, schematic illustration of the electrical connection of the flat coils, and FIG. 4B shows a schematic circuit diagram of the same coil arrangement. The reference symbols used are the same as those used in FIG. 2. The first and the fourth flat coil S1 and, respectively, S4, the turns of said flat coils running with the same winding sense and being connected between the first outer via VA1 and the inner via VI, form a first subgroup UG1. The second and the third flat coil S1, S3, which are wound with the same winding sense and are connected between the inner via VI and the second outer via VA2, form a second subgroup UG2. The turns of the coils of a subgroup therefore run with the same winding sense as one another in each case, wherein the winding sense of the coils of the first subgroup differs from the winding sense of the coils of the second subgroup.

The flat coils S1, S4 of the first subgroup UG1 are connected in parallel to one another. Accordingly, the coils S2, S3 of the second subgroup UG2 are also connected in parallel to one another. The subgroups UG1, UG2 are connected in series to one another. The outer vias VA1, VA2 are connected to the outputs of the AC voltage source 135, the inner via serving only as an internal contact between flat coils.

All of the flat coils are designed to be as identical as possible to one another (identical coil areas, identical number of turns etc.), apart from in respect of the winding sense, and therefore they have the same impedances as far as possible.

If the AC voltage source 135 provides an excitation current I1 with a fixedly prespecified current amplitude, an excitation current I1/n is applied to each flat coil on account of this connection, wherein n is the number of flat coils of a subgroup which are connected in parallel to one another. In the example where n=2, an excitation current I1/2 is therefore applied to each flat coil S1 to S4. As is clear from FIG. 4A, the excitation current flows through each of the flat coils in the same circulation direction, that is to say for example in the counterclockwise direction or in the clockwise direction, at a specified time. As a result, the electromagnetic fields which are generated by the four flat coils which are situated one above the other overlap in an additive manner at the site of the coil group.

It is also possible for each of the subgroups to comprise more than two flat coils, for example three, four, five, six or more flat coils. It is also possible for the subgroups to have different numbers of flat coils, wherein the partial currents which flow through the coils are then distributed differently given an identical coil design. In particular, it is also possible for a subgroup to comprise only one single flat coil.

Figure 5A:
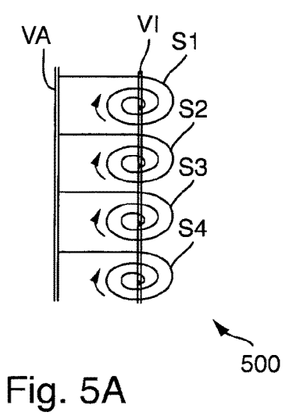
FIGS. 5A and 5B shows, in FIG. 5A, a simplified, schematic illustration of the electrical connection of the flat coils of a coil group with four flat coils which are connected in parallel and are wound with the same winding sense and, in FIG. 5B, a schematic circuit diagram of the same coil arrangement.
Figure 5B:
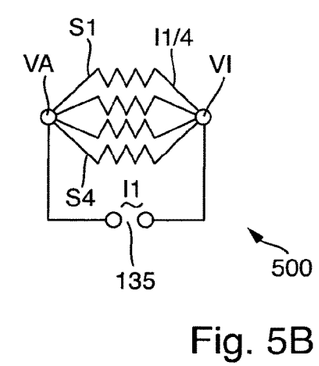

FIGS. 5A and 5B show corresponding illustrations of the coil arrangement and the electrical connection of the flat coils S1 to S4 of a coil group 500 of a multi-layer arrangement of another embodiment. The coil group 500 also has four flat coils S1 to S4 which are situated (vertically) one above the other, the inner terminals of said flat coils being electrically connected to one another by means of a common inner via VI. All of the flat coils are wound with the same winding sense and have outer terminals which are connected to a common outer via VA. The vias VA and VI are connected to the outputs of an AC voltage source 135 for the purpose of operating the coil arrangement. This coil arrangement corresponds to a parallel connection of all four of the flat coils S1 to S4 between the vias VA and VI (compare FIG. 5B).

The excitation current flows through all four of the flat coils S1 to S4 in the same circulation direction at each specified time in this embodiment too, and therefore the generated fields of said coils add up. If an excitation current I1 of a prespecified amplitude is generated by the AC voltage source 135, this excitation current is divided between the vias VA and VI into four partial currents which flow through the respective flat coils. Therefore, only a partial current I1/4 is applied to each flat coil given an identical design of the flat coils and a correspondingly identical impedance. These partial currents are therefore only half the magnitude of the corresponding partial currents in the embodiment according to FIG. 4 given identical current impression.

This shows that dividing flat coils into two (or more) subgroups of flat coils which are each connected in parallel, as is schematically illustrated in FIG. 4, allows an improved degree of efficiency in respect of field generation when power supplies with current impression are used since, given the same prespecified current amplitude, the resulting excitation field strength is greater than in the case of a parallel connection without the flat coils having been divided into subgroups (FIG. 5). In other words, dividing the coils into subgroups makes it possible to achieve a desired excitation field strength with a lower total current amplitude than in the case of a parallel connection without the flat coils having been divided into subgroups.

In addition, the single inner via VI can be used to electrically connect three or more flat coils of a (vertical) coil group without more than one via being required in the interior of the flat coils. As a result, the turn-free inner region of flat coils can be reduced in size in comparison to the prior art and more turns can be accommodated in each coil area. This results in an improved degree of efficiency in respect of the area of the flat coil in comparison to the prior art, and it is therefore possible, for example, for stronger fields to be generated given a prespecified excitation current.

Figure 3B:
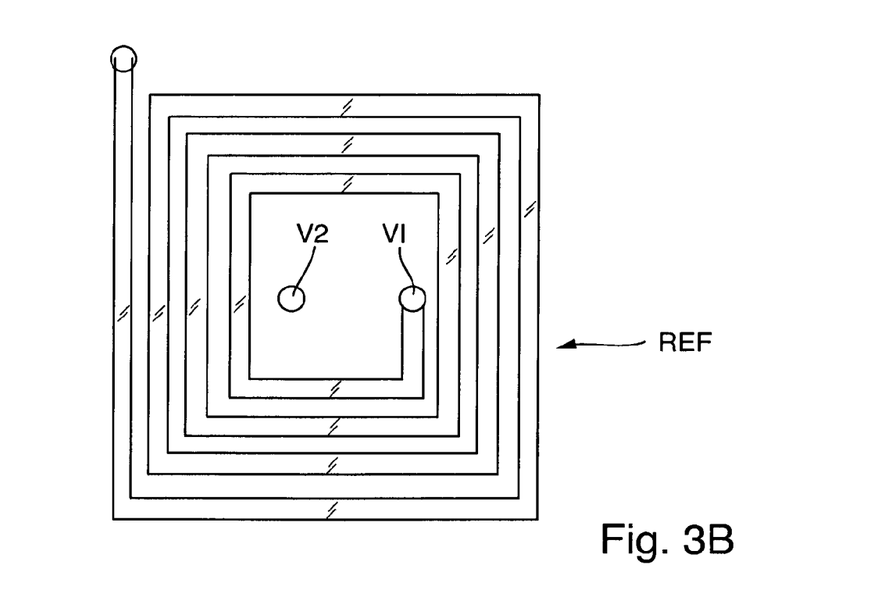

For illustration purposes, FIG. 3B shows a reference flat coil REF according to the prior art in which, in addition to the via VI for the flat coil shown, yet a further via V2 for electrically connecting other flat coils which are arranged above and below said flat coil is provided in the inner region. For comparison purposes, FIG. 3A schematically shows a flat coil S with the same coil area but only one single inner via VI in which there are more turns.

Figure 6A:
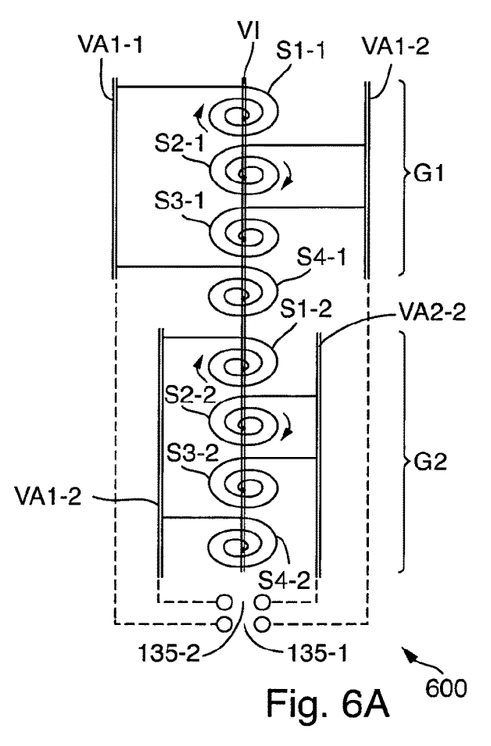
FIGS. 6A and 6B and FIGS. 7A and 7B show schematic coil groups and corresponding schematic circuit diagrams, the flat coils of said coil groups being subdivided into different groups and said groups in turn being subdivided into subgroups.
Figure 6B:
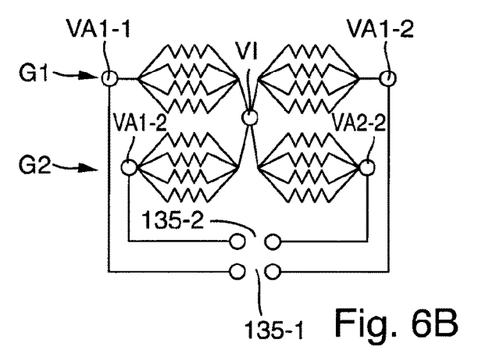
Figure 7A:
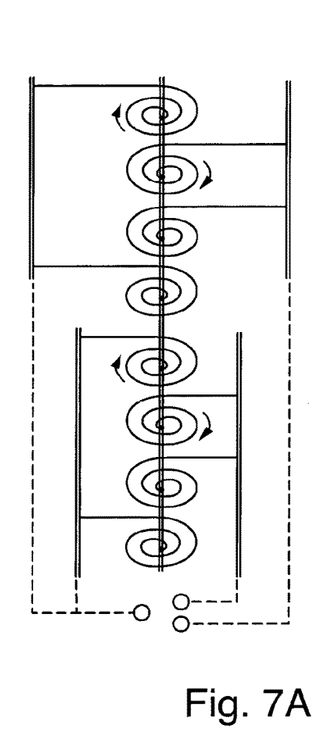
Figure 7B:
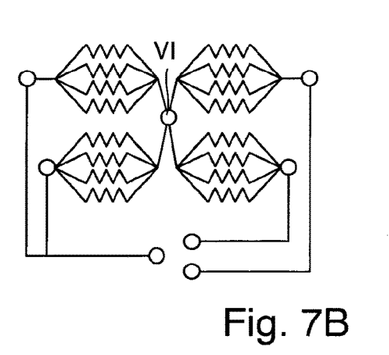

Numerous variants are possible. FIGS. 6 and 7 schematically show examples of coil groups, it being possible for the flat coils of said coil groups to be subdivided into different groups and for said groups in turn to be subdivided into subgroups, but wherein all of the flat coils of a coil group are situated vertically one above the other and are connected by means of a common inner via VI. The embodiments of FIGS. 6 and 7 have the same design as the multi-layer coil arrangement in this case, but wherein different connection options to one or two power supplies are realized.

The design is explained with reference to the coil group 600 in FIG. 6A. The coil group 600 has a total of eight flat coils S1-1 to S4-1 and S1-2 to S4-2 which are arranged (vertically) one above the other. The upper four flat coils S1-1 to S4-1 form a first group G1, the design of said first group being identical to coil group 200 from FIG. 4A. Reference is made to the corresponding description. The corresponding reference symbols are each followed by "-1". A second group G2 of four flat coils is arranged beneath said first group, the design of said second group likewise corresponding to the design of coil group 200 from FIG. 4A. The corresponding components are each provided with the same reference symbols followed by "-2".

All eight of the flat coils are connected by means of a single common inner via VI. Said coils are each divided into first and second subgroups, as described in connection with FIG. 4.

The flat coils of the first group G1 and of the second group G2 can be operated at the same time or with a time delay in relation to one another, for example, by means of a multiplexer. To this end, the flat coils of the first group G1 are connected to a first power supply 135-1 by means of the outer vias VA1-1 and VA2-1. The outer vias VA1-2 and VA2-2 of the second group G2 are connected to a second power supply 135-2 which can be operated electrically independently of the first power supply. As a result, it is possible to adjust the field strengths which are generated by the coil group 600 in a more variable manner by selectively switching on only the first power supply or only the second power supply or by operating both power supplies with a respectively prespecified current amplitude. The flat coils of the different groups can be operated, for example, at different frequencies in order to realize different penetration depths. The connection in FIG. 7A allows selective operation of the first group G1 or of the second group G2.

Multi-layer eddy current probes according to embodiments of the invention provide numerous design options both in respect of the electrical connection of the flat coils to one another and also with regard to optimizing the probe geometries for different applications. It is therefore possible, for example, to produce a multi-layer eddy current probe with a relatively rigid or flexurally stiff multi-layer arrangement, so that the multi-layer eddy current probe acquires a specific prespecified shape, for example an overall planar design. It is also possible to configure multi-layer eddy current probes in a flexible or pliable manner in order to enable the multi-layer eddy current probe to be matched to test object surface shapes which have different curvatures. In both cases, it is possible to construct laterally expanded fields (coil arrays) with the aid of a large number of flat coils, in order to be able to test relatively large surface regions of the test object with flat coils of a relatively small area and therefore with relatively high local resolution.

The invention claimed is:

1. A multi-layer eddy current probe for use in an eddy current test unit for non-destructive testing of electrically conductive materials, comprising:
   a plurality of flat spiral coils which are arranged in different coil layers of a multi-layer arrangement, wherein
   a respective insulating layer which is composed of electrically insulating material is arranged between adjacent coil layers of the multi-layer arrangement,
   each of the flat coils has an inner terminal and an outer terminal,
   selected terminals of selected flat coils of different coil layers are electrically connected to one another by way of vias,
   the flat coils form at least one coil group which has at least three flat coils which are arranged one above the other in different layers, and
   the inner terminals of the at least three flat coils of the coil group are electrically conductively connected by way of a common inner via.

2. The multi-layer eddy current probe as claimed in claim 1, wherein at least two flat coils of the coil group, which flat coils are arranged in different layers, are connected electrically in parallel by way of the inner via and an outer via, wherein turns of these flat coils, which are connected in parallel, run with the same winding sense.

3. The multi-layer eddy current probe as claimed in claim 1, wherein the coil group has at least four flat coils which are arranged one above the other in different layers.

4. The multi-layer eddy current probe as claimed in claim 1, wherein each of the flat coils of the coil group has an inner region which is surrounded by turns, and further wherein only one single inner via of the coil group is arranged in the inner region of each of the flat coils of the coil group.

5. The multi-layer eddy current probe as claimed in claim 1, wherein the turns of the flat coils of the coil group run with the same winding sense, and all of the outer terminals of the flat coils of the coil group are electrically conductively connected by way of a first outer via.

6. The multi-layer eddy current probe as claimed in claim 1, wherein:
   flat coils of the coil group form a first subgroup comprising at least two first flat coils and at least one second subgroup comprising at least two second flat coils,
   turns of the first flat coils run with a same winding sense, and turns of the second flat coils run with a same winding sense and with an opposite winding sense to the turns of the first flat coils;
   outer terminals of the first flat coils are electrically conductively connected by way of a first outer via, and outer terminals of the second flat coils are electrically conductively connected by way of a second outer via.

7. The multi-layer eddy current probe as claimed in claim 1, wherein all of the vias of coil groups of the multi-layer arrangement pass from a first side which is accessible for external contact-connection to an opposite second side which is accessible for external contact-connection.

8. The multi-layer eddy current probe as claimed in claim 1, wherein the multi-layer eddy current probe does not have any buried vias and/or any blind vias.

9. The multi-layer eddy current probe as claimed in claim 1, wherein the multi-layer eddy current probe has a plurality of coil groups which are arranged at a lateral distance next to one another in a one-dimensional or two-dimensional field arrangement.

10. The multi-layer eddy current probe as claimed in claim 1, wherein one or more flat coils of the multi-layer arrangement are provided as measuring coils and are connected to an evaluation device during operation.

11. The multi-layer eddy current probe as claimed in claim 1, wherein the multi-layer arrangement has one or more flat coils which can be used as measuring coils and are arranged substantially coaxially with flat coils of the coil group.

12. An eddy current test unit for non-destructive testing of electrically conductive materials, comprising:
   an electrical power supply; and
   a multi-layer eddy current probe as claimed in claim 1, wherein the multi-layer eddy current probe is connected to an output of the power supply.

13. The eddy current test unit as claimed in claim 12, wherein the electrical power supply is designed to supply excitation current of a prespecified amplitude to field coils of the multi-layer eddy current probe.

14. A multi-layer eddy current probe for use in an eddy current test unit for non-destructive testing of electrically conductive materials, comprising:
   a plurality of flat spiral coils which are arranged in different coil layers of a multi-layer arrangement, wherein
   a respective insulating layer which is composed of electrically insulating material is arranged between adjacent coil layers of the multi-layer arrangement,
   each of the flat coils has an inner terminal and an outer terminal,
   selected terminals of selected flat coils of different coil layers are electrically connected to one another by way of vias,
   the flat coils form at least one coil group which has at least three flat coils which are arranged one above the other in different layers,
   the inner terminals of the at least three flat coils of the coil group are electrically conductively connected by way of a common inner via,
   flat coils of the coil group form a first subgroup comprising at least two first flat coils and at least one second subgroup comprising at least two second flat coils,
   turns of the first flat coils run with a same winding sense, and turns of the second flat coils run with a same winding sense and with an opposite winding sense to the turns of the first flat coils;

outer terminals of the first flat coils are electrically conductively connected by way of a first outer via, and outer terminals of the second flat coils are electrically conductively connected by way of a second outer via.

15. A method for producing a multi-layer eddy current probe which has a multi-layer arrangement comprising a plurality of flat spiral coils which are arranged in different coil layers of the multi-layer arrangement and each have an inner terminal and an outer terminal, wherein a respective insulating layer which is composed of electrically insulating material is arranged between adjacent coil layers, the method comprising the acts of:
   initially, producing all of the coil layers and insulating layers which are situated between the coil layers in a manner situated one above the other without through-plating between coil layers such that a coil group is created at at least one location, said coil group having at least three flat coils which are arranged one above the other in different layers and have inner terminals which are arranged one above the other; and
   thereafter, producing an inner via which passes from the first side to the second side, said inner via connecting the inner terminals of all of the flat coils of the coil group.

\* \* \* \* \*

UNITED STATES PATENT AND TRADEMARK OFFICE
CERTIFICATE OF CORRECTION

PATENT NO. : 10,267,766 B2  
APPLICATION NO. : 14/911945  
DATED : April 23, 2019  
INVENTOR(S) : Timur Kudyakov Page 1 of 1

It is certified that error appears in the above-identified patent and that said Letters Patent is hereby corrected as shown below:

On the Title Page

Item (71) should read:  
(71) Applicant: Magnetische Pruefanlagen GmbH, Reutlingen (DE)

Signed and Sealed this  
Twenty-second Day of October, 2019

Andrei Iancu  
*Director of the United States Patent and Trademark Office*